United States Patent [19]

Rossi et al.

[11] Patent Number: 4,938,389
[45] Date of Patent: Jul. 3, 1990

[54] FILTER BOTTLE

[75] Inventors: Scott R. Rossi, Haverhill; Jeffrey P. Gilbard, Boston, both of Mass.

[73] Assignee: Eye Research Institute of Retina Foundation, Boston, Mass.

[21] Appl. No.: 266,701

[22] Filed: Nov. 3, 1988

[51] Int. Cl.⁵ .................... B65D 5/58; B01D 35/00
[52] U.S. Cl. .................... 222/189; 222/420; 210/321.64; 604/126
[58] Field of Search ............... 222/189, 188, 187, 212, 222/420–422, 476, 190, 215, 206, 211; 604/126; 210/321.64

[56] References Cited

U.S. PATENT DOCUMENTS

| 644,703 | 3/1900 | Buckley. | |
|---|---|---|---|
| 2,626,606 | 1/1953 | Campbell | 128/249 |
| 2,807,288 | 9/1957 | Shea | 141/18 |
| 3,149,758 | 9/1964 | Bush et al. | 222/189 |
| 3,154,074 | 10/1964 | Harrison | 128/232 |
| 3,189,223 | 6/1965 | Mackal | 222/1 |
| 3,323,684 | 6/1967 | Durand et al. | 222/189 |
| 3,335,917 | 8/1967 | Knight | 222/189 |
| 3,756,472 | 9/1973 | Vos | 222/189 |
| 4,441,996 | 4/1984 | Hurst | 210/241 |
| 4,443,336 | 4/1984 | Bennethum | 210/238 |
| 4,463,880 | 8/1984 | Kramer et al. | 222/189 |
| 4,533,068 | 8/1985 | Meierhoefer | 222/189 |
| 4,764,274 | 8/1988 | Miller | 222/189 |
| 4,767,016 | 8/1988 | Cook, Jr. et al. | 222/189 |
| 4,811,866 | 3/1989 | Golias | 222/189 |

FOREIGN PATENT DOCUMENTS 3419572 12/1984 Fed. Rep. of Germany ...... 222/189

Primary Examiner—Michael S. Huppert
Assistant Examiner—Glenn L. Heinl
Attorney, Agent, or Firm—Lahive & Cockfield

[57] ABSTRACT

A multidose liquid dispenser for maintaining the sterility of solutions without a preservative has been developed. The dispenser includes a filter assembly having a hydrophobic filter and a hydrophilic filter in tandem with the hydrophobic filter located near the dispensing tip. The use of the hydrophobic exterior filter and the hydrophilic interior filter permits excellent liquid flow while precluding the growth of bacteria on the filter. The inability of the bacteria to attach to the exterior hydrophobic filter prevents clogging of the pores.

9 Claims, 1 Drawing Sheet

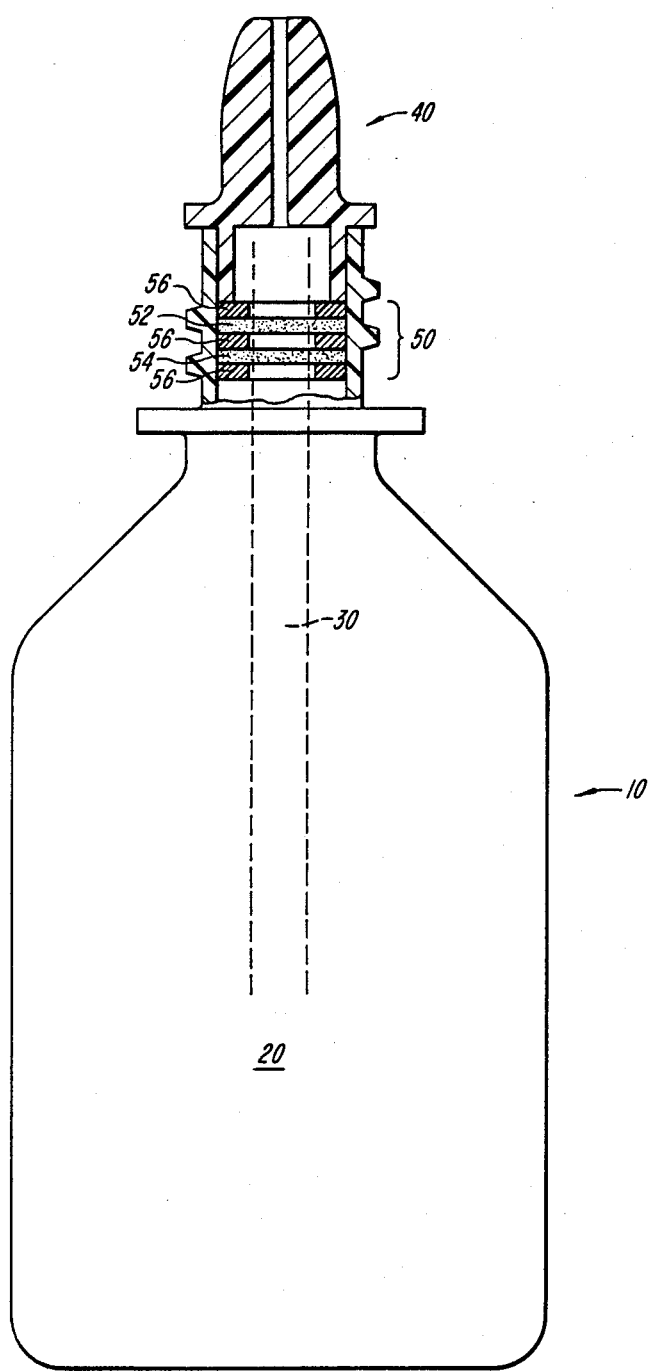

FILTER BOTTLE

BACKGROUND OF THE INVENTION

The present invention concerns a liquid dispenser for sterile solutions. More particularly, the present invention relates to a multidose dispenser for sterile solutions, particularly in a dropwise form, which keeps the solutions aseptic without the use of preservatives.

A number of solutions which are sold and administered as over-the-counter ("OTC") and/or prescription preparations must be kept sterile to prevent bacterial or other microbial growth. The conventional means of Preventing microbial growth is to add a preservative or other antibacterial agent to the solution during packaging. Although these preservatives keep the enclosed solution sterile, the bottle itself may harbor external bacterial growth which is carried along with the outflow of fluid. In addition, the preservatives themselves are often toxic not just to bacteria but also to the cells which are being treated by the bottled preparation. For example, the preservatives used in most eye drops are toxic to goblet cells and other cells in the eye. Because of this toxicity level, continued use can cause more long term problems then the solutions solve.

Filter bottles have been used to store the solutions in aseptic condition after cold sterilization for many years. Antimicrobial filters, e.g., 0.2 micron filters, are often used for this purpose. However, in many of these previous designs, removal of the fluid required removal of the filter. In other cases, the limitations of flow caused by the small pore size of the microbial filters are not important because the solution is not dispensed through the filters or high pressures are available for dispersing. Because of these and the other problems with filter bottles, the use of preservatives or single dose packaging have been the rule in dispensing OTC and other liquid products such as eye medicants or drops.

Accordingly, an object of the invention is to provide a multidose liquid dispenser which can keep solutions aseptic under prolonged use without the use of an antibacterial or antimicrobial additive.

A further object of the invention is to provide a filter bottle for use in cold sterilization processes which provides good flow properties and protection against bacterial contamination.

Another object of the invention is to provide a bottle which can be used for eye drops and similar solutions which do not contain preservatives.

These and other objects and features of the invention will be apparent from the following description and the drawing.

SUMMARY OF THE INVENTION

The present invention features a multidose dispenser for sterile liquids which provides antimicrobial action without need for preservatives or other antibacterial additives. The invention is based, in part, on a dual filter assembly which provides good flow rate of fluids, protection against contamination after filter breakage, and assists in prevention of bacterial growth on the external dispersing tip of the bottle.

The liquid dispenser of the present invention, which is particularly useful for dispensing sterile liquids or solutions, has a reservoir compartment adapted for storing the sterile solutions. The reservoir is in fluid communication, through a flow passage, to a tip adapted to dispense the sterile solution. A filter assembly is sealed across the entire expanse of the flow of passage to prevent fluid delivery except through the filter assembly. The filter assembly contains both a hydrophobic and a hydrophilic filter, the filters being arranged such that the hydrophilic filter is closer to the reservoir while the hydrophobic filter is closer to the liquid dispensing end of the tip. Both the hydrophobic and hydrophilic filters have pores which are of a size sufficient to prevent bacteria from traversing the filter, e.g., the pores act as microbial filters.

In preferred embodiments of the invention, the filter assembly has the hydrophobic and hydrophilic filters separated, e.g., by a support ring. A more preferred embodiment has a filter structure whereby there are a plurality of support rings between, and on opposite sides of, the filters to provide structural support and filter separation. In the most preferred embodiment, the filter assembly is located in the flow passage such that the hydrophobic filter is substantially at the dispensing end of the liquid dispensing tip. The filter assembly can be sealed in the flow passage by any means. Preferred methods of sealing the filter assembly in the flow passage are non-flaking adhesives, ultrasonic sealing, and heat sealing.

BRIEF DESCRIPTION OF THE DRAWING

The sole figure of the drawing shows a cut-away view of a liquid dispenser of the invention.

DESCRIPTION OF THE INVENTION

The present invention features a multidose dispenser for sterile liquids which is capable of preserving sterility of the contained solution without the use of chemical preservatives or antibacterial additives. The dual filter assembly of the present apparatus provides excellent flow properties, inhibits bacterial contamination of the bottle, and preserves the sterility of the contained solution.

The sole figure of the drawing more clearly illustrates that present invention. Flexible squeeze bottle 10 has a reservoir chamber 20 connected by flow path 30 to tip 40. Standard dispersing bottles with removable tip, e.g., low density polypropylene such as those made by Wheaton Scientific, Melville, N.J. can be used. The bottles were modified by addition of filter assembly 50 located across flow path 30 near tip 40. Filter assembly 50 contains a hydrophobic filter 52, for example a TF (PTFE) 0.2 micron pore size filter such as is obtainable from Gelman Sciences, Inc., Ann Arbor, Mich. Hydrophilic filter 54 is a microbial filter, preferably having a pore size of 0.2 microns or less. The FP Vericel filter, also obtainable from Gelman Sciences, Inc., is exemplary of this type of filter. The hydrophilic filter may have a laminated polypropylene web support on one side for reinforcement and durability. Support disks 56 are placed to further support and separate filters 52 and 54. Silicone rings punched from Silicone sheeting, e.g., Silastic Brand Sheeting from Dow Corning, Midland, Mich., can be formed into a preferred ring for use to provide both support and separation functions. The rings are bound to the filters, and to the plastic of the bottle, by standard techniques, e.g., ultrasonic binding, heat sealing, or adhesive sealing. If an adhesive is used, it must be non-flaking. A preferred adhesive is Silastic Brand Medical Adhesive Silicone-type A, also from Dow Corning. The adhesive must be kept off the active portions of the filters to prevent contamination and maintain flow.

The dual filter assembly of the invention has a variety of purposes. First, if there is a break in either filter, sterility is maintained by having two distinct filters. Second, the hydrophobic filter does not retain water so bacteria are inhibited from growing on the outside surface of the filter assembly. Third, the hydrophilic filter closer to the reservoir wets better than the hydrophobic filter, and since flow rate is improved by better wetting, the use of the hydrophilic filter permits a higher flow rate from the bottle without high pressure.

The following non-limiting Examples further illustrate the efficacy of the invention.

EXAMPLE 1

This Example, 15 ml Wheaton bottles with snap-tips are fitted with filter assemblies of the invention. This filter assembly has a 0.2 micron FP Vericel Membrane Filter (Gelman Sciences, Inc.) glued between two punched Silastic rings using Silastic Brand Medical Adhesive Silicone-type A (Dow Corning). The filter disks are 8 mm in diameter and Silastic support rings are also 8 mm disks of Silastic Brand Sheeting (0.02 inches) (Dow Corning) with 5.5 mm essentially central holes punched-out. The assembly further includes a 0.2 micron PTFE membrane filter (Gelman Sciences, Inc.) which is bonded between one of the Silastic rings and a third Silastic ring. The assembly is glued to the snap-tip dropper such that the Silastic support ring is bonded directly to the dispensing end of the snap-tip dropper and the Vericel filter is closest to the solution in the bottle.

Five bottles made with the filter assembly and another bottle, identical except lacking the filter assembly, were filled with substantially the same amount of a test solution under cold sterilization procedures. The solution is an eye drop solution such as described in U.S. Pat. No. 4,775,531, issued on an application of the present inventor. All the bottles were used to dispense fluid to the eyes of human volunteers between one and two times daily for one month, excluding weekends. At the end of the period, the snap-tip assembly was removed and 1 ml of the remaining fluid was placed in fluid thioglycollate broth for fourteen days at 30-35° C. An additional 1 ml of the remaining fluid was placed in soybean-casein digest medium for fourteen days at a temperature of 20-25° C. After the fourteen days, the fluid thioglycollate broth was plated out on soybean-casein digest medium and incubated at 20-25° C. for an additional fourteen days.

At the end of the period, all of the solutions contained within the bottles having the filter assembly were sterile. However, the solution from the bottle without the filter system was contaminated with bacteria as indicated by turbidity of the thioglycollate broth. Further investigation indicated that the bacteria was pseudomonas.

EXAMPLE 2

For this Example, forty-nine filter bottles were made using the filter assembly described in Example 1. The bottles were all filled with the same eye drop solution. Eleven patients were given the bottles at separate time intervals as needed. The patients were instructed to use the drops contained at least six times a day. The bottles were returned with a portion of the solution remaining and compliance was monitored by measuring the volume remaining upon the return of the bottles. Mean duration of usage was $23.4 +/- 1.2$ (SEM) days. Twenty-three of the bottles were used for twenty-eight days or longer. Upon return, all forty-nine solutions tested sterile by USP guidelines, using the testing described in USP XXI, Section 71.

As is clearly indicated by the Examples, the present invention provides a means of maintaining the sterility of solutions without the use of additives such as preservatives or other antibacterial agents. Because of the toxic effects of such agents on certain cells, this has numerous advantages.

The invention is not limited by the foregoing Examples but may be practiced in other obvious variations. Such other variations of the claimed invention are included within the following claims.

What is claimed is:

1. A liquid dispenser for dispensing sterile liquids comprising:
   a reservoir compartment adapted for storing sterile liquids;
   a tip adapted to dispense said sterile liquids;
   a flow passage providing fluid communication between said tip and said reservoir; and
   a filter assembly, said filter assembly being sealed in said fluid passage so that it extends across the entire expanse of said flow passage to prevent fluid and air flow except through said filter assembly, said filter assembly comprising a hydrophilic filter and a hydrophobic filter arranged in fluid communication serially along said flow passage so that said hydrophilic filter is nearer to said reservoir than said hydrophobic filter, said hydrophobic filter and said hydrophilic filter each having pores sufficiently small to act as microbial filters.

2. The liquid dispenser of claim 1 wherein said hydrophobic filter and said hydrophilic filter are separated in said filter assembly.

3. The liquid dispenser of claim 2 wherein said hydrophobic filters and said hydrophilic filters are separated by a support ring.

4. The liquid dispenser of claim 3 wherein said filter assembly comprises a plurality of support 5. The liquid dispenser of claim 1 wherein said filter assembly is located in said flow passage such that said hydrophobic filter is substantially at said liquid dispensing tip.

6. The liquid dispenser of claim 1 wherein said filter assembly is sealed in said flow passage by an adhesive.

7. The flow dispenser of claim 1 wherein said filter assembly is sealed in said flow passage by ultrasonic sealing.

8. The liquid dispenser of claim 1 wherein said filter assembly is sealed in said flow passage by heat sealing.

9. The liquid dispenser of claim 1 wherein said liquid dispenser comprises a multidose dispenser.

* * * * *

UNITED STATES PATENT AND TRADEMARK OFFICE
CERTIFICATE OF CORRECTION

PATENT NO. : 4,938,389

DATED : July 3, 1990

INVENTOR(S) : Scott R. Rossi, et al.

It is certified that error appears in the above-identified patent and that said Letters Patent is hereby corrected as shown below:

At Column 1, line 14 delete "Preventing" and insert --preventing--.

At Column 4, line 49 after the word "support" insert --rings--.

Signed and Sealed this

Twenty-fifth Day of August, 1992

*Attest:*

DOUGLAS B. COMER

*Attesting Officer*     *Acting Commissioner of Patents and Trademarks*